United States Patent [19]

Iizuka et al.

[11] 4,060,457

[45] Nov. 29, 1977

[54] APPARATUS FOR GROWING ANIMAL CELLS

[75] Inventors: Masahiko Iizuka, Fujisawa; Jiro Suzuki; Sigeyasu Kobayashi, both of Kamakura, all of Japan

[73] Assignee: Ichiro Kojima, Tokyo, Japan

[21] Appl. No.: 647,177

[22] Filed: Jan. 7, 1976

[30] Foreign Application Priority Data

Jan. 7, 1975 Japan ............................ 50-4272

[51] Int. Cl.² .................... C12K 9/00; C12K 1/10
[52] U.S. Cl. ....................... 195/127; 195/103.5 V; 23/259; 23/292
[58] Field of Search ............ 195/127, 139, 103.5 R, 195/103.5 V; 23/259, 292

[56] References Cited

U.S. PATENT DOCUMENTS

| 2,967,093 | 1/1961 | Raymond | 23/259 |
| 3,732,149 | 5/1973 | Santero | 195/127 |
| 3,833,341 | 9/1974 | Tocci | 23/259 |
| 3,834,876 | 9/1974 | Kormendy et al. | 23/259 |

Primary Examiner—Alvin E. Tanenholtz
Attorney, Agent, or Firm—Armstrong, Nikaido & Marmelstein

[57] ABSTRACT

An apparatus for growing animal cells of this invention comprises tubes with a hole near bottom of each tube and a variable angle tube holder. Cells may be attached and proliferated in the tubes which contain a nutrient medium, which can be removed simply from the tubes through holes by changing the angle of the tubes. Cell sheets in many tubes can be washed simply, rapidly and simultaneously.

8 Claims, 10 Drawing Figures

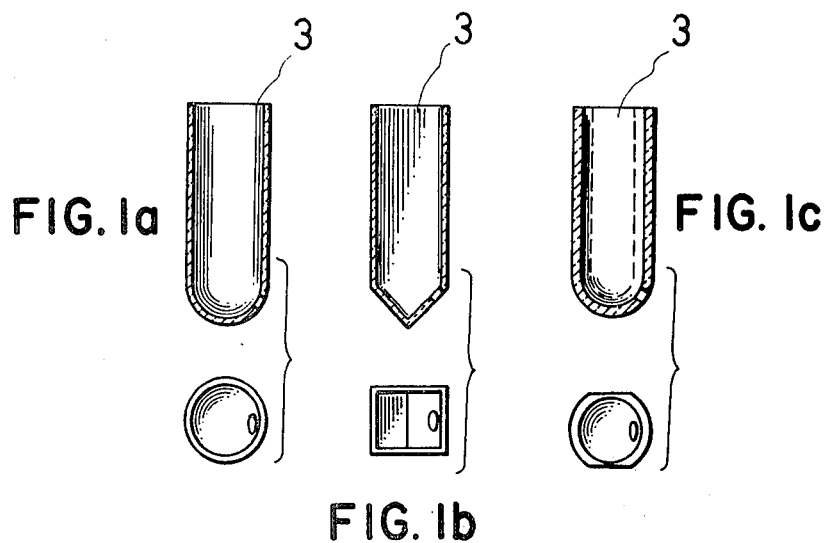
FIG. 1a  FIG. 1c
FIG. 1b
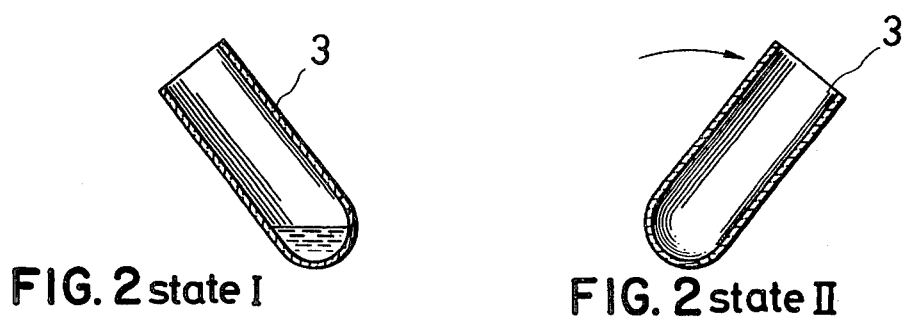
FIG. 2 state I   FIG. 2 state II
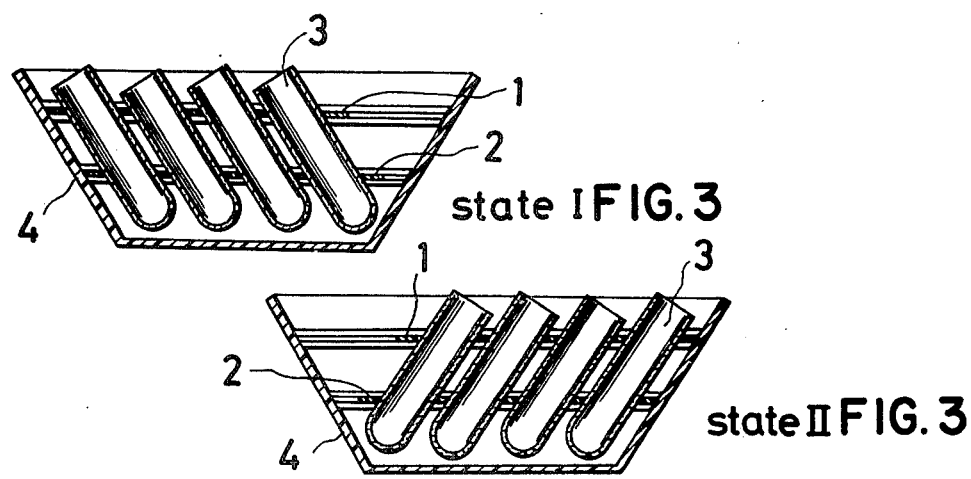
state I FIG. 3
state II FIG. 3

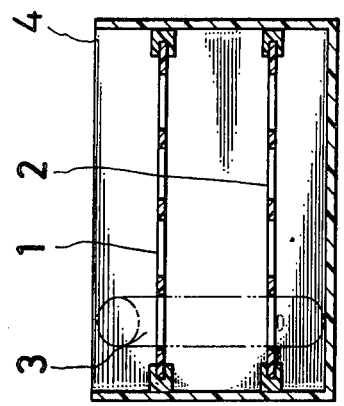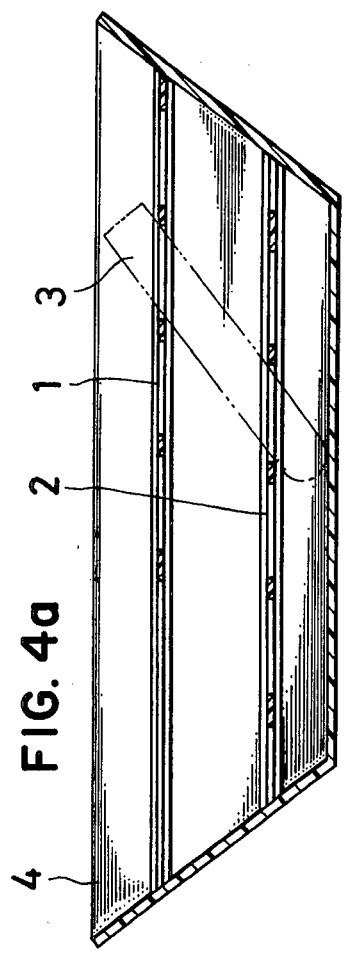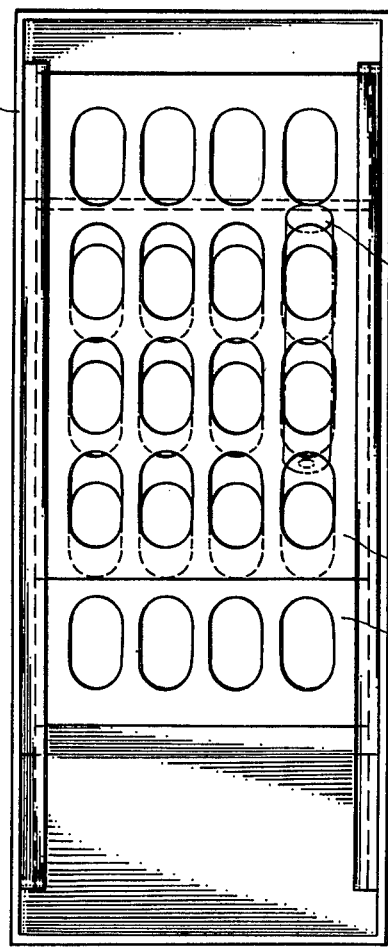

APPARATUS FOR GROWING ANIMAL CELLS

BACKGROUND OF THE INVENTION

This invention relates to a novel, and useful apparatus for growing animal cells, especially an apparatus for growing animal cells in which the animal cells may be treated in many vessels easily, rapidly and simultaneously.

DESCRIPTION OF THE PRIOR ART

The techniques for growing the animal cells in many equivalent vessels have been generally used in the field in biological and pharmaceutical sciences, especially of cell biology, virology and pharmacology. In these techniques, many procedures such as opening and closing many vessels, feeding of liquid into the vessels and removing of the liquid from the vessels, are necessary.

Heretobefore, these procedures had be done with each vessel repeatedly and therefore was very troublesome.

An object of this invention is to overcome the problems and disadvantages of the conventional techniques. A further object of this invention is to provide a suitable apparatus which enables feeding of the liquid to many vessels and removal of the liquid from the vessels in single actions for culturing animal cells in many vessels.

Other objects and advantages of this invention will become apparent hereinafter.

SUMMARY OF THE INVENTION

The objects of this invention may be achieved by providing an apparatus comprising a plurality of small vessels, each of which has a hole near bottom through which liquid can freely pass, and a variable angle vessel holder.

DESCRIPTION OF THE PREFERRED EMBODIMENT

In the culture apparatus of this invention, a small vessel such as a round, angular or flat sided tube with a hole near bottom is used. The apparatus consists of the above tubes, a tube holder in which the angle at which the tubes are held is variable, and a box reservoir in which the above holder with the tubes can be laid. The holder can serve as well for the box reservoir.

FIG. 1. (a), (b) and (c) show a sectional elevation view and plan view of the examples of the tube with a hole near bottom.

FIG. 2, "State I" indicates the state of the above tubes in which a liquid such as a culture medium can be contained, "State II" shows the state of the above tubes in which the liquid can not be contained.

"State I" in FIG. 3 shows the apparatus of this invention in a state with the above tubes 3 in the box 4 containing liquid, "State II" shows the apparatus in a state with the tubes in which the liquid can not be contained.

The tube holder is preferably constituted by upper panel 1 and lower panel 2 which have means to hold each tube in the usual manner and which can be slid holizontally. The upper and lower panels slide parallel with each other, therefore the angle of the held tubes with respect to the horizontal can be arbitrarily varied. When putting the above tubes with the hole near bottom into the tube holder, arranging the holes of the tubes in order on the line of panel sliding, then by sliding the upper and lower panels, the holes of all of the tubes move up and down simultaneously. Thus the tubes with the hole can be set in FIG. 3 "State I" in which the tubes can contain a liquid or can be set in FIG. 3 "State II" in which the tubes can not contain liquid. When the state of this apparatus is changed from "State I" of the FIG. 3 to the "State II" of the FIG. 3, and then efflux from the tubes is aspirated from the arbitrary point of the bottom of the box reservoir or the box tube holder, the liquid such as nutrient medium can be removed rapidly and simultaneously from all the tubes in the holder. Additionally, in the "State II" of the FIG. 3, liquid is poured into the box reservoir or box tube holder, then the state of the tubes in the apparatus is changed to the "State I" of the FIG. 3 and overloaded liquid is aspirated. Following these procedures all the tubes in the holder are dispensed of the liquid. It is of course possible to dispense liquid to each tube in the "State I" of the FIG. 3 by conventional methods. The liquids may be cell suspensions, culture media, solutions of chemicals, virus suspensions, salt solutions, acidic solutions or organic solvents such as alcohols for treating the attached cells.

The tube with a hole in this invention may be made of glass, plastics or other suitable materials upon which animal cells may be attached and proliferated. As to the form of the tubes, the cross sections may be circular as indicated in FIG. I (a) or the cross section may be polygonal such as square as shown in FIG. I (b) or a hybrid of above mentioned two forms such as shown in FIG. I (c). There is no limitation on the length and thickness of the tube with a hole.

However, usually the length of the tube is preferably 2 cm $\sim$ 20 cm, the thickness of the tube is preferably 0.1 mm $\sim$ 3 mm and the diameter of the tube is preferably 5 mm $\sim$ 5 cm. There is also no limitation on the position and area of the hole. However, usually a diameter of 0.5 mm $\sim$ 5 mm is preferable. As to the position of the hole, it placed at the lowest part of the tube when the tube is laid at an angle of 30° $\sim$ 60° with respect to the horizontal.

Variable angle tube holder used in this invention may be made of glass, metals, plastics or composite of these materials. The upper and lower panels may be a plate with holes which can hold tubes, or a composite of wires or sticks. The number of the held tubes is not limited. However, usually 5 $\sim$ 50 tubes are preferably used in one apparatus. As for the box reservoir, it is desired to be transparent, so a box made of glass or plastics may be preferable, FIG. 4 shows an example of the box tube holder. In this example, upper panel 1 and lower panel 2 slide along with the grooves 3 at the inner side of the box.

The cell culture apparatus of this invention is preferably used for growing all kinds of animal cells.

The invention is illustrated by the following examples.

EXAMPLE 1

Tubes of 15 mm diameter, 54 mm length, with a hole of a diameter of 2.5 mm, the position of which is lowest when the angle of the tube is 45° with respect to the horizontal, are set in "State I" of the FIG. 3. To each tube 0.75 $\times$ 10$^5$ cells/0.15 ml of culture media, and 0.15 ml of stepwise dilutions of interferon are dispensed and incubated over night in a $CO_2$ incubator, mean while the cells attach to the bottom of the tubes and are simultaneously affected by interferon. Then the angle of the tubes are changed to "State II" of the FIG. 3, and culture media with interferon are removed from the tubes to box and then aspirated. Subsequently, the tubes are returned to "State I" of the FIG. 3. All the tubes with interferon treated cells and the half the number of the tubes with nontreated cells have added thereto $10^6$ p.f.u. of vericular stomatitis virus and 1.5 μg of actinomycin D/0.3 ml culture media. Another half the number of the tubes with non-treated cells have added thereto 1.5 μg actinomycin D/0.3 ml culture media and treated for one hour. Additionally tritiated uridine (1 μCi/0.2 ml/tube) is added to all the tubes and incubated further for 3 hours, in the meantime a radio isotope is incorporated into VSV specific RNA. Again the state of the tubes are changed to the "State II" of the FIG. 3, and unadsorbed VSV, actinomycin D and 3H-uridine are discarded. Then the box has added thereto enough volume of 5% cold trichloroacetic acid (TCA) solution to dip the cell sheets in the tubes, and stored 30 minutes in the cold to remove low molecular radio labeled uridine. Following repeated washes with TCA solution, the tubes are washed twice with methanol and dried with an infrared lamp or with flower. The thoroughly dried tubes are then put into vials containing toluen scintillator and counted for their polymerized tritiated uridine. Thus from the quantity of radiolabelled VSV specific RNA, viral inhibitory activity of the interferon is estimated.

EXAMPLE 2

Monolayer cell sheets are made in "State I" tubes. Following removal of an old culture media, cells are washed with a new media and a different amount of interferon inducers such as polyinosinic acid - poly cytidilic acid complex or NDV is added, and made to contact with the cells for 1 to 2 hours. After removal of the inducers, the cells are replenished with a new culture media and incubated for various periods. For example, concentration of the inducer is arranged along lateral rows, incubation period after contact is arranged along vertical rows. Thus interferon preparations are formed in various conditions are obtained easily.

EXAMPLE 3

As in example 2, interferon inducers are changed to vacine strain of virus. Thus a determination of optimal condition for viral vaccine production is easily qualified.

What is claimed is:

1. An apparatus for growing animal cells, said apparatus comprising:
    a. a plurality of small vessels, each said vessel having a hole in the lower portion thereof;
    b. a box reservoir; and
    c. vessel holder means including an upper panel and a lower panel mounted in said box reservoir, said upper panel and said lower panel each including holding means for cooperating with each other to hold each of said vessels, wherein at least one of said panels can be moved horizontally with respect to the other of said panels such that the angle of the axis of each said vessel when in said holder means can be set parallel to one another at 30°–60° on either side of the vertical by the horizontal movement of said panels with respect to one another, and wherein said hole is positioned in said vessel such that it is at the lowest point of said vessel when said vessel is tilted to one side of the vertical by said holder means.

2. The apparatus of claim 1 wherein said small vessel is tube having a circular bottom.

3. The apparatus of claim 1 wherein said small vessel is made of glass.

4. The apparatus of claim 1 wherein said box reservoir is transparent.

5. The apparatus of claim 1 wherein said box reservoir is in the shape of a dish.

6. The apparatus of claim 1 wherein said box reservoir has a groove at the side thereof for supporting said panels.

7. The apparatus of claim 1 wherein said box reservoir has two vertical walls parallel to the direction of movement of said panels and walls joining said two vertical walls which are tilted in the direction of tilting of said small vessels.

8. The apparatus of claim 1 wherein said box reservoir and upper and lower panels are transparent and said holding means comprises a plurality of small oval holes in said panels.

* * * * *